(12) United States Patent
Yuyama et al.

(10) Patent No.: US 7,167,353 B2
(45) Date of Patent: Jan. 23, 2007

(54) IONIC LIQUID, METHOD OF DEHYDRATION, ELECTRICAL DOUBLE LAYER CAPACITOR, AND SECONDARY BATTERY

(75) Inventors: Kanako Yuyama, Chiba (JP); Ryutaro Nozu, Chiba (JP); Gen Masuda, Chiba (JP); Takaya Sato, Chiba (JP)

(73) Assignee: Nisshinbo Industries, Inc., Tokyo (JP)

( * ) Notice: Subject to any disclaimer, the term of this patent is extended or adjusted under 35 U.S.C. 154(b) by 0 days.

(21) Appl. No.: 10/484,613

(22) PCT Filed: Apr. 24, 2003

(86) PCT No.: PCT/JP03/05253

§ 371 (c)(1),
(2), (4) Date: Jan. 22, 2004

(87) PCT Pub. No.: WO03/091198

PCT Pub. Date: Nov. 6, 2003

(65) Prior Publication Data

US 2004/0199015 A1 Oct. 7, 2004

(30) Foreign Application Priority Data

Apr. 24, 2002 (JP) .............................. 2002-122180

(51) Int. Cl.
*H01G 9/00* (2006.01)
(52) U.S. Cl. ....................... 361/502; 361/503; 361/504; 361/512; 361/523; 361/525; 361/528; 429/306; 429/307; 252/62.2

(58) Field of Classification Search ........ 361/502–512, 361/516–519, 523–534; 252/62.2; 429/306–307, 429/322; 29/25.03
See application file for complete search history.

(56) References Cited

U.S. PATENT DOCUMENTS

| 4,189,761 | A | * | 2/1980 | Finkelstein et al. | ......... 361/505 |
| 5,621,607 | A | * | 4/1997 | Farahmandi et al. | ........ 361/502 |
| 5,969,936 | A | * | 10/1999 | Kawasato et al. | .......... 361/502 |
| 6,280,883 | B1 | * | 8/2001 | Lamanna et al. | ........... 429/307 |

(Continued)

FOREIGN PATENT DOCUMENTS

JP 3-91688 A 4/1991

(Continued)

OTHER PUBLICATIONS

New Battery Solvents and Electrolytes, Denki Kagaku, vol. 48, No. 12, pp. 665-671 (1980) (copy and partial translation).

(Continued)

*Primary Examiner*—Nguyen T. Ha
(74) *Attorney, Agent, or Firm*—Birch, Stewart, Kolasch & Birch, LLP (57) ABSTRACT

The water present within an ionic liquid that is in a liquid state at 25° C. or an organic solution containing at least one ionic compound is decomposed by bringing electrodes into contact with the ionic liquid or organic solution within an atmosphere having a dew-point temperature not higher than −40° C. or under a reduced pressure of not more than 75 torr, thereby reducing the water content. This process makes it possible to obtain highly dehydrated ionic liquids.

7 Claims, 5 Drawing Sheets

U.S. PATENT DOCUMENTS

| | | | |
|---|---|---|---|
| 6,445,567 B1 * | 9/2002 | Komatsuki et al. | 361/518 |
| 6,783,896 B2 * | 8/2004 | Tsujioka et al. | 429/307 |
| 2004/0094741 A1 * | 5/2004 | Sato et al. | 252/1 |

FOREIGN PATENT DOCUMENTS

| | | | |
|---|---|---|---|
| JP | 10-64540 A | 3/1998 | |
| JP | 10-116631 A | 5/1998 | |
| JP | 10-338653 A | 12/1998 | |
| JP | 11-297355 A | 10/1999 | |
| JP | 2001-106656 A | 4/2001 | |
| JP | 2002-75443 A | 3/2002 | |
| JP | 2002-99001 A | 4/2002 | |
| JP | 2002-110472 A | 4/2002 | |

OTHER PUBLICATIONS

Material Stage, vol. 3, No. 1, pp. 73-77 (2003) (copy and partial translation).

Certificate regarding presentation made by Gen Masuda, Kentaro Takagi, Takaya Sato and Masaaki Isobe at the Meeting of the 70th Anniversary of the Electrochemical Society of Japan on Apr. 1, 2003.

Certificate regarding presentation made by Gen Masuda, Kentaro Takagi, Takaya Sato and Masaaki Isobe at the Meeting of the 83rd Spring Meeting of The Chemical Society of Japan on Mar. 18, 2003.

Certificate regarding presentation made by Takaya Sato at the 1st meeting of The Committee of Capacitor Technology of The Electrochemical Society of Japan on Jan. 24, 2003.

* cited by examiner

IONIC LIQUID, METHOD OF DEHYDRATION, ELECTRICAL DOUBLE LAYER CAPACITOR, AND SECONDARY BATTERY

TECHNICAL FIELD

The present invention relates to ionic liquids and a method of dehydration thereof, and also to electrical double-layer capacitors and secondary cells.

BACKGROUND ART

Ionic compounds generally form crystals composed of positively charged cations and negatively charged anions which pull electrostatically on each other. For example, when the ionic compound NaCl is dissolved in water, water molecules surround the Na$^+$ ions (cations) and the Cl$^-$ ions (anions) that make up the crystals, turning each ion into a large overall ion. Because the large ions that form in this way are unable to approach each other, the electrostatic interactions therebetween weaken, enabling the cations and anions to move freely throughout the solution as particles carrying their respective charges.

In this way, ionic compounds dissolve in water and various other liquids to form liquids that conduct electricity, i.e., electrolytic solutions. Electrolytic solutions prepared by dissolving an ionic compound in an organic solvent are commonly used in nonaqueous electrolyte batteries and capacitors.

When NaCl is subjected to a rise in temperature and thermal motion is activated to such an extent as to overcome interactions between the ions, this compound itself becomes a liquid capable of conducting electricity. In the case of NaCl, the transformation of this solid into a liquid occurs at an elevated melting point of 800° C. An ionic compound or salt thereof that has melted in this way is generally called a fused salt.

The chemical species present in fused salts are all charge-bearing cations or anions; no neutral atoms or molecules are present. Accordingly, in a fused salt, elements that cannot be obtained from ordinary aqueous electrolytic solutions because the reducing power or oxidizing power with respect to water is too strong (i.e., metals such as alkali metals, aluminum and rare-earth elements, and non-metals such as fluorine) can be electrolyzed and thereby obtained in uncombined form. This is the principal industrial application of fused salts.

Among the above-described fused salts, there are some which remain in a liquid state even at room temperature and do not solidify at very low temperatures. Such fused salts which remain in a liquid state at room temperature or below are referred to in particular as "room-temperature fused salts" or "ionic liquids."

These ionic liquids have a number of characteristics, including: (1) a vapor pressure that is either nonexistent or very low, (2) non-flammability or fire-retarding properties, (3) ionic conductivity, (4) a higher decomposition voltage than water, (5) a broader liquid temperature range than water, and (6) handleability in air.

Such characteristics are put to good use by employing these ionic liquids as novel electrolytes capable of being utilized at room temperature or lower in a variety of applications, including the electrodeposition of metals or alloys, electrolytic plating baths, electrolytes for energy-storing electrochemical devices, and as solvents for organic synthesis.

Of these applications, ionic liquids having a minimal water content are required particularly for use as nonaqueous electrolytes or as organic solvents in reactions that must be conducted in a water-free system.

Quaternary ammonium salts are generally prepared by the quaternization of a tertiary amine with, for example, an alkyl halide, a dialkyl sulfate or a dialkyl carbonate. Moreover, when changing the anionic species, synthesis is carried out via the quaternary ammonium hydroxide by neutralization with an inorganic acid or an organic acid. The quaternary ammonium carbonate or hydroxide salt used as the starting material for obtaining a quaternary ammonium salt by such a method is generally available commercially in the form of an aqueous solution or an alcohol solution. To reduce the water content therein, use has typically been made of a process in which the aqueous or alcohol solution is evaporated to dryness and the quaternary ammonium salt is removed as a solid, then is purified by recrystallization.

However, when a quaternary ammonium salt is industrially evaporated to dryness, it takes a long time to completely eliminate moisture, in addition to which the quaternary ammonium salt undergoes thermal degradation during heating.

A number of processes have been developed to avoid such problems, including a method in which, instead of removing the moisture completely, a solvent such as ethanol is added and concentration and recrystallization are carried out to lower the moisture content (JP-A 2001-106656), methods that involve storing the electrolyte or organic solvent produced in a low-humidity environment (JP-A 10-116631, JP-A 10-64540), a method in which a solute containing residual moisture is dissolved in an organic solvent and an inert gas is bubbled through the resulting solution to remove the moisture (JP-A 10-338653), and methods involving the use of desiccants.

However, moisture removal by recrystallization, drying with a desiccant or bubbling through an inert gas relies on resources such as alcohols, molecular sieves or nitrogen gas which are either difficult to reuse or for which a method of reuse must be established. Hence, moisture removal in this way is poorly suited for mass production. On the other hand, in methods involving storage in a low-humidity environment, it takes quite a long time to lower the moisture level.

In the case of quaternary ammonium salts which are solid at ambient temperature, such as $(CH_3)_4N \cdot BF_4$ and $(CH_3)_3(C_2H_5)N \cdot BF_4$, the moisture content can be lowered to about 10 to 20 ppm by vacuum drying crystals of the salt. However, in attempts that have been made to lower the moisture content in ionic liquids of relatively high viscosity using the above techniques, the lowest moisture content achieved has been about 200 ppm, and this was by dehydration carried out on a small amount of ionic liquid in a laboratory setting. When a large amount of ionic liquid is dehydrated at one time in a factory, for example, the percent reduction in moisture content worsens dramatically.

By making use of a method in which first the ionic liquid $(CH_3)(C_2H_5)_2(CH_3OC_2H_4)N \cdot BF_4$ is dissolved in an organic solvent, then nitrogen gas is bubbled through the solution, the water content in the solution can be lowered to about 50 ppm. However, the salt concentration is difficult to adjust, making this approach inappropriate in cases where a specific concentration is required.

When an ionic liquid or a solution prepared by dissolving an ionic liquid in an organic solvent is used as a liquid electrolyte in an electrical storage device such as a lithium ion secondary cell or an electrical double-layer capacitor, to ensure the polar properties and longevity of the electrodes,

"it is desirable for the moisture within the solvent to be lowered to less than about 30 ppm" (*Denki Kagaku* 48, No. 12, 665–671 (1980)). Hence, liquid electrolytes that have been subjected to a high degree of dehydration are required.

The present invention was conceived of in light of the above circumstances. One object of the invention is to provide highly dehydrated ionic liquids. Another object of the invention is to provide a method of dehydrating ionic liquids. Further objects are to provide electrical double-layer capacitors and secondary cells which use such ionic liquids.

DISCLOSURE OF THE INVENTION

The inventors have conducted extensive investigations in order to achieve the above objects. As a result, they have found that the water present in ionic liquids or ionic liquid-containing solutions can be electrolyzed in an atmosphere having a dew-point temperature not higher than −40° C. or under a reduced pressure of not more than 76 torr to give a highly dehydrated ionic liquid or ionic compound-containing solution. This discovery led ultimately to the present invention.

Accordingly, the invention provides the following.
(1) An ionic liquid containing cations and anions, which liquid is characterized by having a water content of not more than 150 ppm and being in a liquid state at a temperature not above 25° C.
(2) The ionic liquid of (1) above which is characterized by having a water content of not more than 50 ppm.
(3) The ionic liquid of (1) or (2) above which is characterized by being an onium salt.
(4) The ionic liquid of (3) above which is characterized in that the cation is a quaternary ammonium ion of general formula (1) below (wherein $R^1$ to $R^3$ are each independently an alkyl of 1 to 5 carbons, and any two from among $R^1$, $R^2$ and $R^3$ may together form a ring; and R' is methyl or ethyl).
(5) The ionic liquid of (4) above which is characterized in that the quaternary ammonium ion is $(CH_3)(C_2H_5)_2(CH_3OC_2H_4)N^+$.
(6) The ionic liquid of any one of (1) to (5) above which is characterized in that the anion is at least one selected from among $BF_4^-$, $PF_6^-$, $ClO_4^-$, $CF_3SO_3^-$, $CF_3CO_2^-$ and $(CF_3SO_2)_2N^-$, and has a theoretical decomposition voltage of at least 1.23 V.
(7) A method of dehydration which is characterized by bringing electrodes into contact with an ionic liquid that is in a liquid state at 25° C. within an atmosphere having a dew-point temperature not higher than −40° C. or under a reduced pressure of not more than 76 torr so as to effect the decomposition of water present in the ionic liquid.
(8) A method of dehydration which is characterized by bringing electrodes into contact with an organic solution containing one or more ionic compound within an atmosphere having a dew-point temperature not higher than −40° C. or under a reduced pressure of not more than 76 torr so as to effect the decomposition of water present in the organic solution.
(9) The method of dehydration of (8) above which is characterized in that the ionic compound is at least one selected from among alkali metal salts, quaternary ammonium salts, quaternary phosphonium salts and transition metal salts.
(10) The method of dehydration of any one of (7) to (9) above which is characterized by stirring the ionic liquid or the organic solution at the time of contact with the electrodes.
(11) The method of dehydration of any one of (7) to (10) above which is characterized in that the electrodes are composed of a positive electrode and a negative electrode, the positive electrode containing a metal which has an equilibrium potential with ions, an oxide or a peroxide of the same metal that is not less than 0.4 V versus the normal hydrogen electrode (NHE) and the negative electrode containing a metal which has an equilibrium potential with ions of the same metal that is not less than −0.8 V versus the normal hydrogen electrode (NHE); and in that a voltage is applied across the positive and negative electrodes which is not less than the sum of the theoretical decomposition voltage for water of 1.23 V, the oxygen overvoltage $\eta_{O2}$ (in V) at the positive electrode, the hydrogen overvoltage $\eta_{H2}$ (in V) at the negative electrode and the resistance component iR (wherein i stands for the current density and R is the resistance component) (in V).
(12) The method of dehydration of (11) above which is characterized in that the positive electrode contains at least one selected from among platinum, rhodium, palladium, iridium, silver, gold, aluminum, aluminum oxide, osmium oxide, silver oxide, tin oxide and titanium oxide; and in that the negative electrode contains at least one selected from among platinum, rhodium, palladium, iridium, copper, silver, gold, aluminum, actinium, bismuth, cobalt, mercury, nickel, iron, polonium, tin and technetium.
(13) An electrical double-layer capacitor having a pair of polarizable electrodes, a separator between the polarizable electrodes and a liquid electrolyte, which electrical double-layer capacitor is characterized in that the liquid electrolyte contains the ionic liquid of any one of (1) to (6) above and an organic solvent having a water content of not more than 50 ppm.
(14) A secondary cell having a positive electrode, a negative electrode, a separator between the positive and negative electrodes, and a liquid electrolyte, which secondary cell is characterized in that the liquid electrolyte contains the ionic liquid of any one of (1) to (6) above and an organic solvent having a water content of not more than 50 ppm.
(15) An electrical double-layer capacitor having a pair of polarizable electrodes, a separator between the polarizable electrodes and a liquid electrolyte, which electrical double-layer capacitor is characterized in that the liquid electrolyte is an ionic liquid or an organic solution containing one or more ionic compound which has been dehydrated by the method of dehydration according to any one of (7) to (12) above.
(16) A secondary cell having a positive electrode, a negative electrode, a separator between the positive and negative electrodes, and a liquid electrolyte, which secondary cell is characterized in that the liquid electrolyte is an ionic liquid or an organic solution containing one or more ionic compound which has been dehydrated by the method of dehydration according to any one of (7) to (12) above.

BRIEF DESCRIPTION OF THE DIAGRAMS

BEST MODE FOR CARRYING OUT THE INVENTION

The invention is described more fully below.

[Ionic Liquid]

The ionic liquid of the invention contains cations and anions, has a water content of not more than 150 ppm, and is in a liquid state at a temperature not higher than 25° C.

The cations are not subject to any particular limitation, although quaternary ammonium ions or quaternary phosphonium ions are preferred. Specific preferred examples are quaternary ammonium ions of formula (1) below.

(1)

In formula (1), $R^1$ to $R^3$ are each independently an alkyl of 1 to 5 carbons, and any two from among $R^1$, $R^2$ and $R^3$ may together form a ring. R' is methyl or ethyl.

Exemplary alkyls having 1 to 5 carbons in formula (1) include methyl, ethyl, propyl, 2-propyl, butyl and pentyl. The viscosity of the ionic liquid tends to increase as the molecular weight becomes larger. At a high viscosity, it may be difficult to achieve a high degree of dehydration. It is thus preferable for at least one of the groups $R^1$ to $R^3$ to be methyl, ethyl or propyl, and especially methyl or ethyl.

Exemplary cations in which any two groups from among $R^1$ to $R^3$ form a ring include quaternary ammonium ions containing an aziridine, azetidine, pyrrolidine or piperidine ring.

Of these, $(CH_3)(C_2H_5)_2(CH_3OC_2H_4)N^+$ is especially preferred because it is easy to synthesize and handle, in addition to which it has a low viscosity and a low melting point.

No particular limitation is imposed on the anions. Illustrative examples include $BF_4^-$, $PF_6^-$, $AsF_6^-$, $SbF_6^-$, $AlCl_4^-$, $HSO_4^-$, $ClO_4^-$, $CH_3SO_3^-$, $CF_3SO_3^-$, $CF_3CO_2^-$, $(CF_3SO_2)_2N^-$, $Cl^-$, $Br^-$ and $I^-$. The selection of at least one anion from among $BF_4^-$, $PF_6^-$, $ClO_4^-$, $CF_3SO_3^-$ and $(CF_3SO_2)_2N^-$ is preferred because these have an excellent degree of dissociation, stability and ion mobility, a broad potential window, and a relatively low liquid resistance that makes handling easy.

In cases where the water content is lowered by the subsequently described dehydration method, it is preferable for the cations to be $(CH_3)(C_2H_5)_2(CH_3OC_2H_4)N^+$, for the anions to be at least one selected from among $BF_4^-$, $PF_6^-$, $ClO_4^-$, $CF_3SO_3^-$, $CF_3CO_2^-$ and $(CF_3SO_2)_2N^-$, and for the ionic liquid to have a theoretical dissociation voltage of at least 1.23 V.

As noted above, the ionic liquid of the invention has a water content of not more than 150 ppm. However, for use in such applications as nonaqueous electrolytes and solvents for reactions that must be conducted in a water-free system, it is advantageous for the ionic liquid to have a water content of not more than 100 ppm, preferably not more than 50 ppm, more preferably not more than 40 ppm, yet more preferably not more than 30 ppm, even more preferably not more than 25 ppm, and most preferably not more than 10 ppm.

The ionic liquid is one which is liquid at a temperature of not above 25° C. However, to enable advantageous use as an electrolyte salt in electrical storage devices used at low temperatures and as a solvent for low-temperature reactions, it is preferable for the ionic liquid to be one which is liquid at a temperature of not above 15° C., and especially not above 0° C.

One way in which the ionic liquid composed of the foregoing quaternary ammonium salt can be prepared is described. First, a tertiary amine is mixed with, for example, an alkyl halide or a dialkyl sulfate, and the mixture is heated, if necessary, to form a quaternary ammonium halide. In cases where a compound of low reactivity is used, such as an alkoxyethyl halide or an alkoxymethyl halide, it is desirable to carry out the reaction under applied pressure, such as in an autoclave, and under heating, if necessary.

The resulting quaternary ammonium halide is dissolved in an aqueous solvent such as water and subjected to anion exchange by neutralization via the hydroxide salt as described above, or reacted with a reagent that generates the required anionic species, such as silver tetrafluoroborate or silver tetrafluorophosphate, so as to effect an anion exchange reaction, thereby yielding a quaternary ammonium salt.

The above-described ionic liquid of the invention has numerous advantages: (1) a vapor pressure that is either nonexistent or very low, (2) non-flammability or fire-retarding properties, (3) ionic conductivity, (4) a higher decomposition voltage than water, (5) a broader liquid temperature range than water, (6) handleability in air, (7) a very low water content, and (8) a broader potential window than hitherto known organic ionic liquids.

Accordingly, the ionic liquid can of course be used in conventional applications for ionic liquids. Moreover, because it has a very low water content, it is highly suitable for use as an electrolyte in electrical storage devices. In particular, because it has a broad potential window, even when it is used as an electrolyte in lithium ion secondary cells, unlike prior-art imidazolium-based ionic liquids, there is no chance of the electrolyte or electrolytic solution undergoing oxidative or reductive decomposition.

Moreover, most reaction solvents widely used in organic synthesis, such as benzene, methylene chloride and ether, are volatile substances which are carcinogenic or otherwise harmful to the human body. By contrast, the ionic liquids of the invention are reaction solvents for organic synthesis which have a very low volatility and can be repeatedly reused. Moreover, because of their low water content, they can be used as organic solvents for reactions that must be conducted in a water-free system, and are thus capable of contributing as well to the field of green chemistry where new synthetic processes that have less of an environmental impact are being developed.

[Method of Dehydration]

In the method of dehydration according to the invention, electrodes are brought into contact with an ionic liquid that is in a liquid state at 25° C. or with an organic solution containing one or more ionic compound, within an atmosphere having a dew-point temperature of not higher than −40° C. or under a reduced pressure of not more than 76 torr, so as to effect the decomposition of water present in the ionic liquid or the organic solution.

As used herein, "ionic compound" is a concept that includes both liquid-state salts and solid-state salts. Although not subject to any particular limitation, the use of one or more selected from among alkali metal salts, quaternary ammonium salts, quaternary phosphonium salts and transition metals is preferred.

Specific, non-limiting examples of organic solvents that can be used when preparing the organic solution include nitrites such as acetonitrile and propionitrile; acyclic ethers such as dibutyl ether, 1,2-dimethoxyethane, 1,2-ethoxymethoxyethane, methyl diglyme, methyl triglyme, methyl tetraglyme, ethyl glyme, ethyl diglyme, butyl diglyme, and glycol ethers (e.g., ethyl cellosolve, ethyl carbitol, butyl cellosolve, butyl carbitol); heterocyclic ethers such as tetrahydrofuran, 2-methyltetrahydrofuran, 1,3-dioxolane and 4,4-dimethyl-1,3-dioxane; butyrolactones such as γ-butyrolactone, γ-valerolactone, δ-valerolactone, 3-methyl-1,3-oxazolidin-2-one and 3-ethyl-1,3-oxazolidin-2-one; and other solvents commonly used in electrochemical devices, such as amide solvents (e.g., N-methylformamide, N,N-dimethylformamide, N-methylacetamide, N-methylpyrrolidinone), carbonate solvents (e.g., diethyl carbonate, dimethyl carbonate, ethyl methyl carbonate, propylene carbonate, ethylene carbonate, styrene carbonate), and imidazolidinone solvents (e.g., 1,3-dimethyl-2-imidazolidinone). Any one or mixtures of two or more of these solvents may be used.

In the above method of dehydration, moisture within the system is reduced by decomposition. However, if the system at the same time takes up moisture from the outside atmosphere, a marked decline occurs in the moisture removal efficiency. It is thus essential for the system exterior to be a dry atmosphere having a dew-point temperature of not more than −40° C. or to be evacuated to a reduced pressure of not more than 76 torr.

To increase the moisture removal efficiency, the dew-point temperature is set to preferably not more than −50° C., more preferably not more than −60° C., and most preferably not more than −80° C.; or the degree of vacuum is set to a pressure of preferably not more than 10 torr, and most preferably not more than 1 torr.

Moreover, because water is not itself composed of ions and the only means for transferring water within the system onto the electrode surfaces is diffusion, it is preferable to stir the ionic liquid or the organic solvent in order to shorten the time required for removing moisture from the system.

The speed of the stirrer during stirring is not subject to any particular limitation, although moisture can be removed more rapidly by setting the speed to 50 to 400 rpm, and especially 200 to 400 rpm.

The electrodes are made up of a positive electrode and a negative electrode. The positive electrode preferably contains a metal having an equilibrium potential with ions, an oxide or a peroxide of the same metal which is not less than 0.4 V versus the normal hydrogen electrode (NHE). The negative electrode preferably contains a metal having an equilibrium potential with ions of the same metal which is not less than −0.8 V versus the normal hydrogen electrode. It is preferable for a voltage to be applied across the positive and negative electrodes which is not less than the sum of the theoretical decomposition voltage for water of 1.23 V, the oxygen overvoltage $\eta_{O2}$ (in V) at the positive electrode, the hydrogen overvoltage $\eta_{H2}$ (in V) at the negative electrode and a resistance component iR (wherein i stands for the current density and R is the resistance component) (in V).

That is, the electrode reactions represented by the formulas shown below are known to occur when water is hydrolyzed. It is undesirable to use materials which give rise to a charge transfer $M \rightarrow M^+ + e^-$ (where M is a metal or metal oxide) at the metal in the positive electrode at a potential of not more than 1.229 V versus the normal hydrogen electrode in the presence of $H^+$ (acidity) and at a potential of not more than 0.401 V versus the normal hydrogen electrode in the presence of $OH^-$ (basicity) and which form into ions and dissolve. It is also undesirable to use materials which generate ions in other oxidation reactions.

Moreover, it is preferable to use as the metal in the negative electrode a material which has an equilibrium potential with ions of the same metal of at least 0.000V versus the normal hydrogen electrode in the presence of $H^+$ (acidity) and of at least −0.828 V versus the normal hydrogen electrode in the presence of $OH^-$ (basicity).

Electrode Reactions During Decomposition of Water (1) in the presence of $H^+$:

$$2H^+ + 2e^- \rightarrow H_2 \quad (E^0 = 0.000 \text{V vs. } NHE)$$

$$O_2 + 4H^+ + 4e^- \rightarrow 2H_2O \quad (E^0 = 1.229 \text{ V vs. } NHE)$$

(2) in the presence of $OH^-$ $$2H_2O + 2e^- \rightarrow 2OH^- + H_2 \quad (E^0 = -0.828 \text{ V vs. } NHE)$$

$$O_2 + 2H_2O + 4e^- \rightarrow 4OH^- \quad (E^0 = 0.401 \text{ V vs. } NHE)$$

The positive and negative electrodes may be positive and negative electrodes containing any metallic materials which satisfy the above conditions for the positive and negative electrodes. Preferred examples of the positive electrode include at least one selected from among platinum, rhodium, palladium, iridium, silver, gold, aluminum, aluminum oxide, osmium oxide, silver oxide, tin oxide and titanium oxide. Preferred examples of the negative electrode include at least one selected from among platinum, rhodium, palladium, iridium, copper, silver, gold, aluminum, actinium, bismuth, cobalt, mercury, nickel, iron, polonium, tin and technetium. The above metals may be unalloyed metals or metal alloys.

Preferred combinations of the above positive electrode and the negative electrode include the following.

(1) Positive electrode: aluminum; Negative electrode: aluminum
(2) Positive electrode: aluminum oxide; Negative electrode: aluminum
(3) Positive electrode: silver; Negative electrode: aluminum
(4) Positive electrode: aluminum; Negative electrode: a metal or alloy containing at least one selected from among nickel, iron, cobalt and chromium
(5) Positive electrode: aluminum oxide; Negative electrode: a metal or alloy containing at least one selected from among nickel, iron, cobalt and chromium (6) Positive electrode: silver; Negative electrode: a metal or alloy containing at least one selected from among nickel, iron, cobalt and chromium.

To impart an electrode potential which will elicit a water decomposing reaction, it is necessary to apply across the positive and negative electrodes a voltage which is larger than the theoretical decomposition voltage for water of 1.23 V by exactly the sum of the oxygen overvoltage $\eta_{O2}$ (in V) at the positive electrode, the hydrogen overvoltage $\eta_{H2}$ (in V) at the negative electrode and a resistance component iR (wherein i stands for the current density and R is the resistance component) (in V). Applying a voltage not less than this combined voltage from an external power supply will cause moisture removal via water decomposition to proceed.

The inventive method of dehydration can be carried out by a technique like that described below, although the electrode materials, construction of the electrolytic cell and other conditions are not limited to those specified in the following example and may be altered insofar as the objects of the invention are achievable.

First, the positive electrode used as one of the electrodes is fabricated by cutting an aluminum sheet having an oxidized and etched surface to a given size and spot welding aluminum tape thereon. The negative electrode is similarly fabricated by cutting a nickel sheet to a given size and spot welding nickel tape thereon. An electrolytic cell is then formed by fixing the electrode sheets within a cylindrical glass vessel or the like at a specific interval therebetween.

Next, an ionic liquid or the like is poured into the cell under a dry atmosphere having a dew-point temperature of not more than −40° C., and preferably not more than −50° C. While stirring the ionic liquid at a speed of 50 to 400 rpm, the electrodes are connected to a power source and electricity is passed through at an upper limit current density of 1 to 5 mA/cm² and a voltage setting that is gradually raised from the water decomposing theoretical voltage of 1.23 V to a final voltage of 6 to 8 V over a period of 1 to 24 hours, thereby electrolyzing the water within the system.

In addition to water within the electrical double-layer capacitor or lithium ion secondary cell system, the presence of metallic ions (e.g., iron, chromium, and nickel) capable of provoking electrode reactions within the electrode potential range used is known to lower the capacity and life of the device and to increase undesirable effects such as self-discharge. The above-described dehydration method can also be employed to electrodeposit such metal ions that are present within the system onto the negative electrode.

[Electrical Double-Layer Capacitor]

The electrical double-layer capacitor according to the invention has a pair of polarizable electrodes, a separator between the polarizable electrodes and a liquid electrolyte. The liquid electrolyte is (1) the above-described ionic liquid in combination with an organic solvent having a water content of not more than 50 ppm, or (2) either an ionic liquid or an organic solution containing one or more ionic compound, which ionic liquid or organic solution has been dehydrated by the above-described method of dehydration.

Exemplary organic solvents having a water content of not more than 50 ppm include any of the various solvents mentioned above without particular limitation, provided they can be used in liquid electrolytes for electrical double-layer capacitors.

In the organic solution containing one or more ionic compound, if the ionic compound in the solution is not an ionic liquid, no particular limitation is imposed on the concentration of the compound, although a concentration of 0.1 to 5.0 mol/L, and especially 1.0 to 4.0 mol/L, is preferred. At a concentration of less than 0.1 mol/L, energy loss may rise due to increased internal resistance. On the other hand, at a concentration of more than 5.0 mol/L, undesirable effects such as deposition of the ionic compound and reduced stability may occur at low temperatures.

The polarizable electrodes may be ones produced by coating a current collector with a polarizable electrode composition containing a carbonaceous material and a binder polymer.

The carbonaceous material is not subject to any particular limitation. Illustrative examples include carbonaceous materials prepared by the carbonization of a suitable starting material, and subsequent activation of the carbonized material to yield activated carbon. Examples of suitable starting materials include plant-based materials such as wood, sawdust, coconut shells and pulp spent liquor; fossil fuel-based materials such as coal and petroleum fuel oil, as well as fibers spun from coal or petroleum pitch obtained by the thermal cracking of such fossil fuel-based materials or from tar pitch; and synthetic polymers, phenolic resins, furan resins, polyvinyl chloride resins, polyvinylidene chloride resins, polyimide resins, polyamide resins, polycarbodiimide resins, liquid-crystal polymers, plastic waste and reclaimed tire rubber.

The activation treatment method is not subject to any particular limitation. Use may be made of various methods, including chemical activation and steam activation.

The carbonaceous material used in the invention may be in any of various forms, including shredded material, granulated material, pellets, fibers, felt, woven fabric or sheet.

A conductive material may be added to the above-described carbonaceous material. The conductive material may be any suitable material capable of conferring electrical conductivity to the carbonaceous material. Illustrative, non-limiting, examples include carbon black, Ketjenblack, acetylene black, carbon whiskers, carbon fibers, natural graphite, artificial graphite, titanium oxide, ruthenium oxide, and metallic fibers such as aluminum or nickel. Any one or combinations of two or more thereof may be used. Of these, Ketjenblack and acetylene black, both of which are types of carbon black, are preferred.

The binder polymer may be any polymer suitable for use in the present application. For example, (I) unsaturated polyurethane compounds, (II) polymeric materials having an interpenetrating network structure or a semi-interpenetrating network structure, (III) thermoplastic resins containing units of general formula (2) below (wherein the letter r is from 3 to 5, and the letter s is an integer which is ≧5), and (IV) fluoropolymer materials. Of these binder polymers, the use of polymeric materials (I) to (III) results in a high adhesion, and can therefore increase the physical strength of the electrodes. Fluoropolymer materials (IV) have excellent thermal and electrical stability.

The polarizable electrode composition can be prepared by placing the following ingredients in a mixing vessel and wet mixing: the above-described carbonaceous material (including, if necessary, a conductive material), a binder solution obtained by rendering the binder polymer into solution form, and an optional solvent.

It is preferable to add the binder polymer in an amount, per 100 parts by weight of the carbonaceous material, of 0.5 to 20 parts by weight, and especially 1 to 10 parts by weight.

The above-described polarizable electrode composition is coated onto current conductors to form the polarizable electrodes. Any positive and negative electrode current collectors commonly used in electrical double-layer capacitors may be selected and used for this purpose. The positive electrode current collector is preferably aluminum foil or aluminum oxide, and the negative electrode current collector is preferably copper foil, nickel foil or a metal foil covered on the surface with a copper plating film or a nickel plating film.

The foils making up the respective current collectors may be in any of various shapes, including thin foils, flat sheets, and perforated, stampable sheets. The foil has a thickness of generally about 1 to 200 μm.

Alternatively, the polarizable electrodes can be produced by melting, and blending the polarizable electrode composition, then extruding the blend as a film.

The separator may be one that is commonly used in electrical double-layer capacitors. Illustrative examples include polyolefin nonwoven fabric, polytetrafluoroethylene porous film, kraft paper, sheet laid from a blend of rayon fibers and sisal hemp fibers, manila hemp sheet, glass fiber sheet, cellulose-based electrolytic paper, paper made from rayon fibers, paper made from a blend of cellulose and glass fibers, and combinations thereof in the form of multilayer sheets.

The electrical double-layer capacitor of the invention can be assembled by stacking, fan-folding or winding an electrical double-layer capacitor assembly composed of the above-described pair of polarizable electrodes with a separator therebetween. The capacitor assembly is then formed into a coin-like shape and placed within a battery housing such as a can or a laminate pack, following which it is filled with liquid electrolyte and mechanically sealed if it is a can or heat-sealed if it is a laminate pack.

The above-described electrical double-layer capacitors of the invention are highly suitable for use as low-current electrical storage devices, including memory backup power supplies for electronic equipment such as cell phones, notebook computers and wireless terminals, power supplies for cell phones and portable audio equipment, uninterruptible power supplies for personal computers, and in combination with photovoltaic power generation or wind power generation as load-leveling power supplies. Electrical double-layer capacitors which are capable of being charged and discharged at a large current are well-suited for use as large-current electrical storage devices requiring a large current in such applications as electric cars and electric power tools.

[Secondary Cells]

The secondary cell according to the invention has a positive electrode and a negative electrode, a separator between the positive and negative electrodes and a liquid electrolyte. The liquid electrolyte is (1) the above-described ionic liquid in combination with an organic solvent having a water content of not more than 50 ppm, or (2) either an ionic liquid or an organic solution containing one or more ionic compound, which ionic liquid or solution has been dehydrated by the above-described method of dehydration.

The type of organic solvent used and the concentration of the ionic compound are the same as mentioned above in connection with electrical double-layer capacitors.

The positive electrode active material making up the positive electrode is suitably selected according to the intended use of the electrode, the type of battery and other considerations. For example, positive electrode active materials that may be used in lithium secondary cells and lithium ion secondary cells include chalcogen compounds capable of lithium ion insertion and extraction, and lithium ion-containing chalcogen compounds.

Examples of chalcogen compounds capable of lithium ion insertion and extraction include $FeS_2$, $TiS_2$, $MoS_2$, $V_2O_6$, $V_6O_{13}$ and $MnO_2$.

Specific examples of such lithium ion-containing chalcogen compounds include $LiCoO_2$, $LiMnO_2$, $LiMn_2O_4$, $LiMo_2O_4$, $LiV_3O_8$, $LiNiO_2$ and $Li_xNi_yM_{1-y}O_2$ (wherein M is one or more metal element selected from among cobalt, manganese, titanium, chromium, vanadium, aluminum, tin, lead and zinc; $0.05 \leq x \leq 1.10$; and $0.5 \leq y \leq 1.0$).

The negative electrode active material making up the negative electrode is selected as appropriate for the intended use of the electrode, the type of battery and other considerations. For example, negative electrode active materials that may be used in lithium secondary cells and lithium ion secondary cells include alkali metals, alkali metal alloys, the oxides, sulfides and nitrides of periodic table group 8, 9, 10, 11, 12, 13, 14 and 15 elements capable of lithium ion insertion and extraction, and carbonaceous materials capable of reversibly inserting and extracting lithium ions.

Examples of suitable alkali metals include lithium, sodium and potassium. Examples of suitable alkali metal alloys include metallic lithium, Li—Al, Li—Mg, Li—Al—Ni, sodium, Na—Hg and Na—Zn.

Illustrative examples of oxides of at least one element selected from among periodic table group 8 to 15 elements which are capable of lithium ion insertion and extraction include tin silicon oxide ($SnSiO_3$), lithium bismuth oxide ($Li_3BiO_4$) and lithium zinc oxide ($Li_2ZnO_2$).

Illustrative examples of such sulfides include lithium iron sulfides ($Li_xFeS_2$ ($0 \leq x \leq 3$)) and lithium copper sulfides ($Li_xCuS$ ($0 \leq x \leq 3$)).

Illustrative examples of such nitrides include lithium-containing transition metal nitrides, such as $Li_xM_yN$ (wherein M is cobalt, nickel or copper; $0 \leq x \leq 3$; and $0 \leq y \leq 0.5$), and lithium iron nitride ($Li_3FeN_4$).

Illustrative examples of carbonaceous materials capable of reversibly inserting and extracting lithium ions include graphite, carbon black, coke, glassy carbon, carbon fibers and sintered bodies obtained from any of these.

The binder polymer used in the positive and negative electrodes, the method of fabricating the positive and negative electrodes, and the separator used are all the same as those described above in connection with electrical double-layer capacitors.

The above-described secondary cell can be obtained by stacking, fan-folding or winding a cell assembly composed of the above-described positive electrode and negative electrode with a separator therebetween. The cell assembly is formed into a coin-like shape, placed within a cell housing such as a can or a laminate pack, and filled with the above-described liquid electrolyte, following which the housing is mechanically sealed if it is a can or heat-sealed if it is a laminate pack.

If necessary, reaction-curable substances such as (meth)acrylates, epoxy group-bearing compounds and thermoset urethanes may be added to the liquid electrolyte, and reacted to effect curing.

The above-described secondary cell of the invention can operate at a high capacity and high current without a loss in its excellent characteristics, including charge/discharge efficiency, energy density, output density and life. Moreover, it has a broad service temperature range, and is thus highly suitable for use in a variety of applications, including main power supplies and memory backup power supplies for portable electronic equipment such as video cameras, notebook computers, cell phones and "personal handyphone systems" (PHS), uninterruptible power supplies for equipment such as personal computers, in electric cars and hybrid cars, and together with solar cells as energy storage systems for solar power generation.

EXAMPLE

The following synthesis examples, examples of the invention and comparative examples are provided to illustrate the invention and do not in any way limit the invention.

Synthesis Example 1

Synthesis of $(CH_3)(C_2H_5)_2(CH_3OC_2H_4)N^+.BF_4^-$

A mixed solution prepared by mixing together 100 ml of diethylamine (Kanto Chemical Co., Inc.) and 85 ml of 2-methoxyethyl chloride (Kanto Chemical) was placed in an autoclave and reacted at 120° C. for 12 hours. The internal pressure during the reaction was 0.283 MPa (2.9 kgf/cm$^2$). This yielded a mixture of deposited crystals and reaction solution to which was added, following the 12 hours of reaction, 200 ml of an aqueous solution prepared by dissolving 40 g of sodium hydroxide (Katayama Chemical Inc.) in 200 ml of water. Each of the two divided organic phases that formed as a result was separated off with a separatory funnel and subjected twice to extraction with 250 ml of tetrahydrofuran (Wako Pure Chemical Industries, Ltd.). The separated organic phases were then combined and washed with a saturated saline solution, following which potassium carbonate (Wako Pure Chemical Industries) was added to remove water and vacuum filtration was carried out. The solvent in the resulting organic phase was distilled off in a rotary evaporator, after which the residue was subjected to normal-pressure distillation, yielding 21 g of 2-methoxyethyldiethylamine.

Next, 8.2 g of the 2-methoxyethyldiethylamine was dissolved in 10 ml of tetrahydrofuran (Wako Pure Chemical Industries), then 4.0 ml of methyl iodide (Wako Pure Chemical Industries) was added under ice cooling. After 30 minutes, the mixture was removed from the ice bath and stirred overnight at room temperature. The solvent in this reaction solution was subsequently driven off by vacuum distillation, and the resulting solids were recrystallized from an ethanol (Wako Pure Chemical Industries)—tetrahydrofuran system, yielding 16 g of 2-methoxyethyldiethylmethylammonium iodide.

Next, 15.0 g of the 2-methoxyethyldiethylmethylammonium iodide and 10.7 g of silver tetrafluoroborate (Tokyo Kasei Kogyo Co., Ltd.) were mixed, yielding 11.5 g of $(CH_3)(C_2H_5)_2(CH_3OC_2H_4)N^+.BF_4^-$ (referred to hereinafter as "ionic liquid X") which was a liquid at room temperature (25° C.).

Synthesis Example 2

Synthesis of $(CH_3)(C_2H_5)_2(CH_3OC_2H_4)N^+.(CF_3SO_2)_2N^-$ (Abbreviated Below as DEME$^+$.TFSI$^-$)

First, 10.0 g of the iodine salt of 2-methoxyethyldiethylmethylammonium was dissolved in 50 mL of acetonitrile (Kanto Chemical Co., Ltd.). Next, 9.5 g of lithium trifluoromethanesulfonimide (Kishida Chemical Co., Ltd.) was added to the solution and completely dissolved, following which the solution was stirred for 15 minutes.

The acetonitrile was then removed by vacuum distillation, after which water was added to the residue. Each of the two divided organic phases that formed as a result was washed five times with water, thereby removing impurities from the organic phases.

The washed organic phases were placed under a vacuum with a vacuum pump to thoroughly drive off water, thereby obtaining 6.8 g of DEME$^+$.TFSI$^-$ which was a liquid at room temperature.

Synthesis Example 3

Synthesis of Thermoplastic Polyurethane Resin

A reactor equipped with a stirrer, a thermometer and a condenser was charged with 64.34 parts by weight of preheated and dehydrated polycaprolactone diol (Praccel 220N, made by Daicel Chemical Industries, Ltd.) and 28.57 parts by weight of 4,4'-diphenylmethane diisocyanate. The reactor contents were stirred and mixed for 2 hours at 120° C. under a stream of nitrogen, following which 7.09 parts by weight of 1,4-butanediol was added to the mixture and the reaction was similarly effected at 120° C. under a stream of nitrogen. When the reaction reached the point where the reaction product became rubbery, it was stopped. The reaction product was then removed from the reactor and heated at 100° C. for 12 hours. Once the isocyanate group absorption peak was confirmed to have disappeared from the infrared absorption spectrum, heating was stopped, yielding a solid polyurethane resin.

The resulting polyurethane resin had a weight-average molecular weight (Mw) of $1.71 \times 10^5$. A polyurethane resin solution was prepared by dissolving 8 parts by weight of this polyurethane resin in 92 parts by weight of N-methyl-2-pyrrolidone.

Example 1

Dehydration of Ionic Liquid X

Using as the positive electrode an aluminum sheet having an oxidized and etched surface (30CB, made by Japan Capacitor Industrial Co., Ltd.; thickness, 0.030 mm) that was cut to a size of 20.0×10.0 mm and to which 3.0 mm wide aluminum tape had been spot-welded and using as the negative electrode Cermet #8 (made of nickel and having a thickness of 1.6 mm; produced by Sumitomo Electric Industries, Ltd.) cut to a size of 20.0×10.0 mm and to which 3.0 mm wide nickel tape had been spot-welded, an electrolytic cell was fabricated by fixing the electrodes within a cylindrical glass vessel with the electrodes separated by a distance of about 20.0 mm.

About 5.0 ml of ionic liquid X was poured into the electrolytic cell at an ambient temperature of about 25° C. and in a dry atmosphere having a dew-point temperature of −50° C. While stirring the liquid with a magnetic stirrer at a speed of 100 rpm, a stabilized power supply (PA18-6A, made by Kenwood KK) was connected to the electrodes and electricity was passed through for a period of 24 hours at an upper limit current of 10.0 mA and a voltage setting that was gradually increased from the theoretical water decomposition voltage of 1.23 V to a final voltage of 6.0 V.

The water content of the ionic liquid X that was dehydrated in this way was measured using a Karl Fischer moisture titrator (NKC-610N, manufactured by Kyoto Electronics Manufacturing Co., Ltd.).

Examples 2 to 9

Aside from using the ionic liquids or the alkylammonium salt or lithium salt-containing organic solutions shown in Table 1 instead of ionic liquid X, dehydration was carried out in the same way as in Example 1, following which the water content was measured.

Comparative Example 1

Ionic liquid X was dehydrated by bubbling through nitrogen gas at an ambient temperature of about 25° C. and in a dry atmosphere having a dew-point temperature of −50° C., following which the water content was measured using the above-mentioned moisture titrator.

Comparative Example 2

Ionic liquid X was left to stand at an ambient temperature of about 25° C. in a dry atmosphere having a dew-point temperature of −50° C., following which the water content was measured using the above-mentioned moisture titrator.

The water contents of the ionic liquids and the ionic compound-containing organic solutions in each of the above examples and comparative examples after passing electricity through for 24 hours were measured. The results are shown in Table 1.

Figure 1:
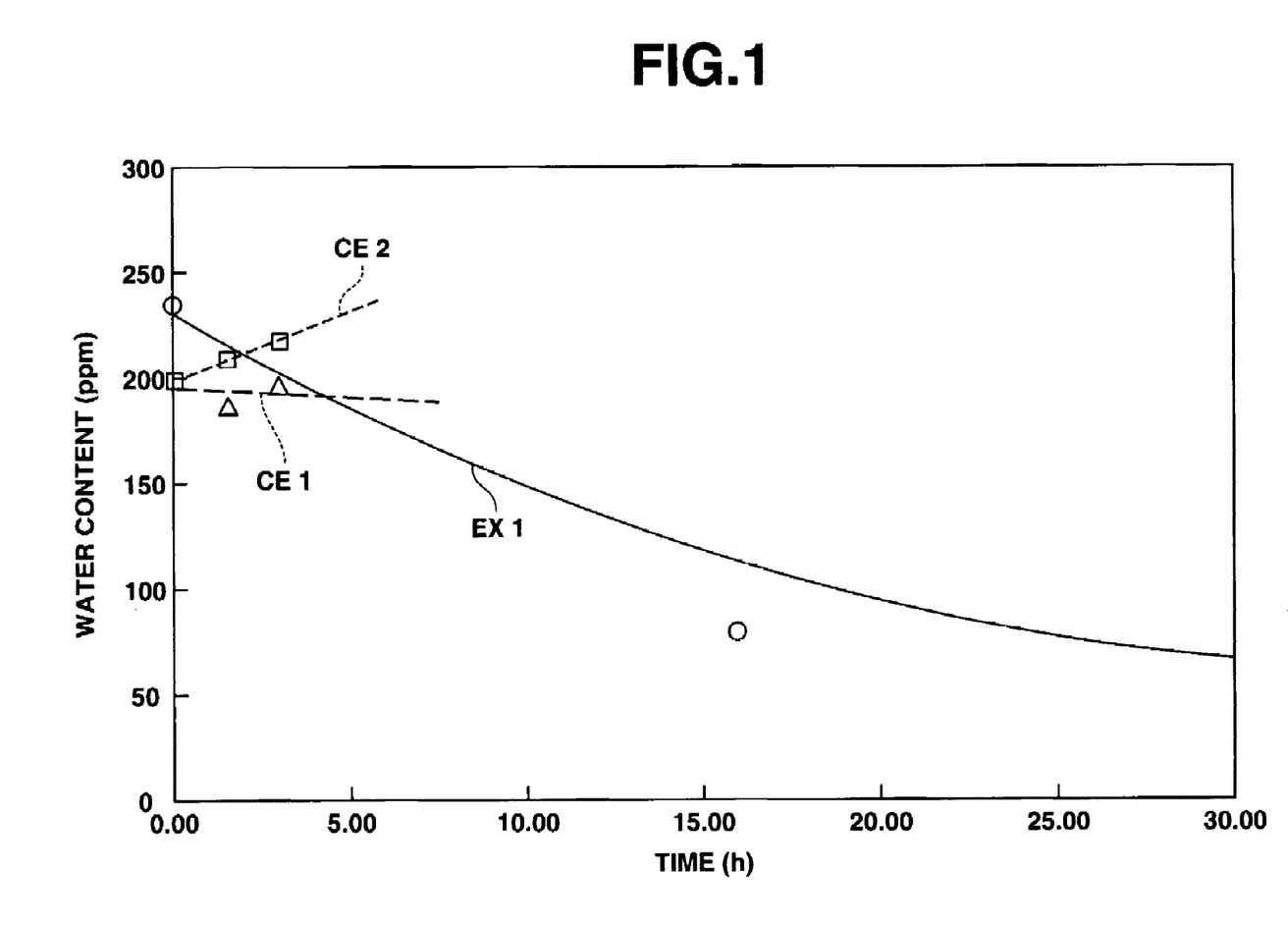
FIG. 1 is a graph showing the change over time in the water content of ionic liquid X in Example 1 according to the invention and in Comparative Examples 1 and 2.

FIG. 1 shows the change over time in the water contents in Example 1 of the invention and in Comparative Examples 1 and 2.

TABLE 1

| | Liquid component | Water content before dehydration (ppm) | Water content after dehydration (ppm) |
|---|---|---|---|
| Example 1 | ionic liquid X | 200 | 50 |
| Example 2 | DEME$^+$.TFSI$^-$ | 300 | 30 |
| Example 3 | EMI$^+$.BF$_4^-$ | 500 | 50 |
| Example 4 | 1.0M EMI$^+$.BF$_4^-$/PC | 50 | 10 |
| Example 5 | 1.0M TEMA$^+$.BF$_4^-$/PC | 50 | 10 |
| Example 6 | 1.0M DEME$^+$.BF$_4^-$/PC | 100 | 10 |
| Example 7 | 1.0M EMI$^+$.PF$_6^-$/PC | 200 | 10 |
| Example 8 | 1.0M EMI$^+$.TFS$^-$/PC | 200 | 10 |
| Example 9 | 1.0M LiPF$_6$/PC | 50 | 10 |
| Comparative Example 1 | ionic liquid X | 200 | 190 |
| Comparative Example 2 | ionic liquid X | 200 | 240 |

In Table 1, the DEME$^+$.TFIS$^-$ prepared in Synthesis Example 2 was used. The DEME$^+$.BF$_4^-$/PC was a solution prepared by dissolving the ionic liquid X obtained in Synthesis Example 1 in propylene carbonate (PC) to a concentration of 1.0 M.

The EMI$^+$.BF$_4^-$, EMI$^+$.BF$_4^-$/PC, EMI$^+$.PF$_6^-$/PC and EMI$^+$.TFS$^-$/PC were 1-ethyl-3-methylimidazolium tetrafluoroborate (EMI$^+$.BF$_4^-$), 1-ethyl-3-methylimidazolium hexafluorophosphate (EMI$^+$.PF$_6^-$) and 1-ethyl-3-methylimidazolium trifluoromethanesulfonate (EMI$^+$.TFS$^-$) (all products of Aldrich Chemical Co., Ltd.), either used directly as supplied or in the form of solutions prepared by dissolution in propylene carbonate to a concentration of 1.0 M.

The LiPF$_6$/PC was a solution of LiPF$_6$ (Kishida Chemical Co., Ltd.) dissolved in propylene carbonate to a concentration of 1.0 M.

The 1.0M TEMA$^+$.BF$_4^-$/PC was a product of Tomiyama Pure Chemical Industries, Ltd. that was used as supplied without modification.

Example 10, Comparative Example 3

Electrical Double-Layer Capacitors

Electrical double-layer capacitors were fabricated as described below using a solution prepared by dissolving the ionic liquid X used in Example 1 and Comparative Example 2 within propylene carbonate to a concentration of 1.0 M as the liquid electrolyte.

First, a slurry was prepared by mixing activated carbon (MSP-20, made by Kansai Netsukagaku K.K.), a conductive material (Denka Black HS100, made by Denki Kagaku Kogyo K.K.) and a binder polymer (PVdF900, made by Kureha Chemical Industry Co., Ltd.) in a weight ratio of activated carbon/conductive material/binder=100:3:5 as the filling substances with N-methylpyrrolidone (NMP, grade 1 product made by Katayama Chemical Inc.) as the solvent in a (filling substance)/NMP weight ratio of 100:212.5. The slurry was applied onto a 30 CB Al/AlO$_x$ sheet (250×150× 0.030 mm) (made by Japan Capacitor Industrial Co., Ltd.) to a width of 90 mm, then dried (80° C.) and rolled (packing density, about 0.7 g/cm$^3$), following which 12 mm diameter disks were punched from the coated sheet for use as the electrodes.

Electrodes having a thickness of about 0.13 mm were selected as the positive electrodes, and electrodes having a thickness of about 0.15 mm were selected as the negative electrodes.

The above-described positive and negative electrodes and two cellulose separators punched to a diameter of 22.0 mm (TF40-35, made by Nippon Kodoshi Corporation; thickness, 0.035 mm) were each impregnated with the liquid electrolyte, then subjected to a vacuum of about 60 torr. The two separators were placed between the electrodes to form a cell, which was then set up together with a three-electrode coin cell jig (Test Cell HS-3E, made by Hohsen Corporation), giving an electrical double-layer capacitor.

The above electrical double-layer capacitor was charged at a current of 1.0 D (1.8 mA) and a voltage setting of 2.5 V, following which it was discharged at 0.2 D, 1.0 D, 3.0 D, 10.0 D and 30.0 D, and the current dependence of the discharge energy was evaluated. The results are shown in FIG. 2.

In the above-described electrical double-layer capacitor, the charging voltage during charging at the above-indicated current level was increased from 2.50 to 4.00 V, following which the discharge energy was evaluated. The results are shown in FIG. 3.

Figure 2:
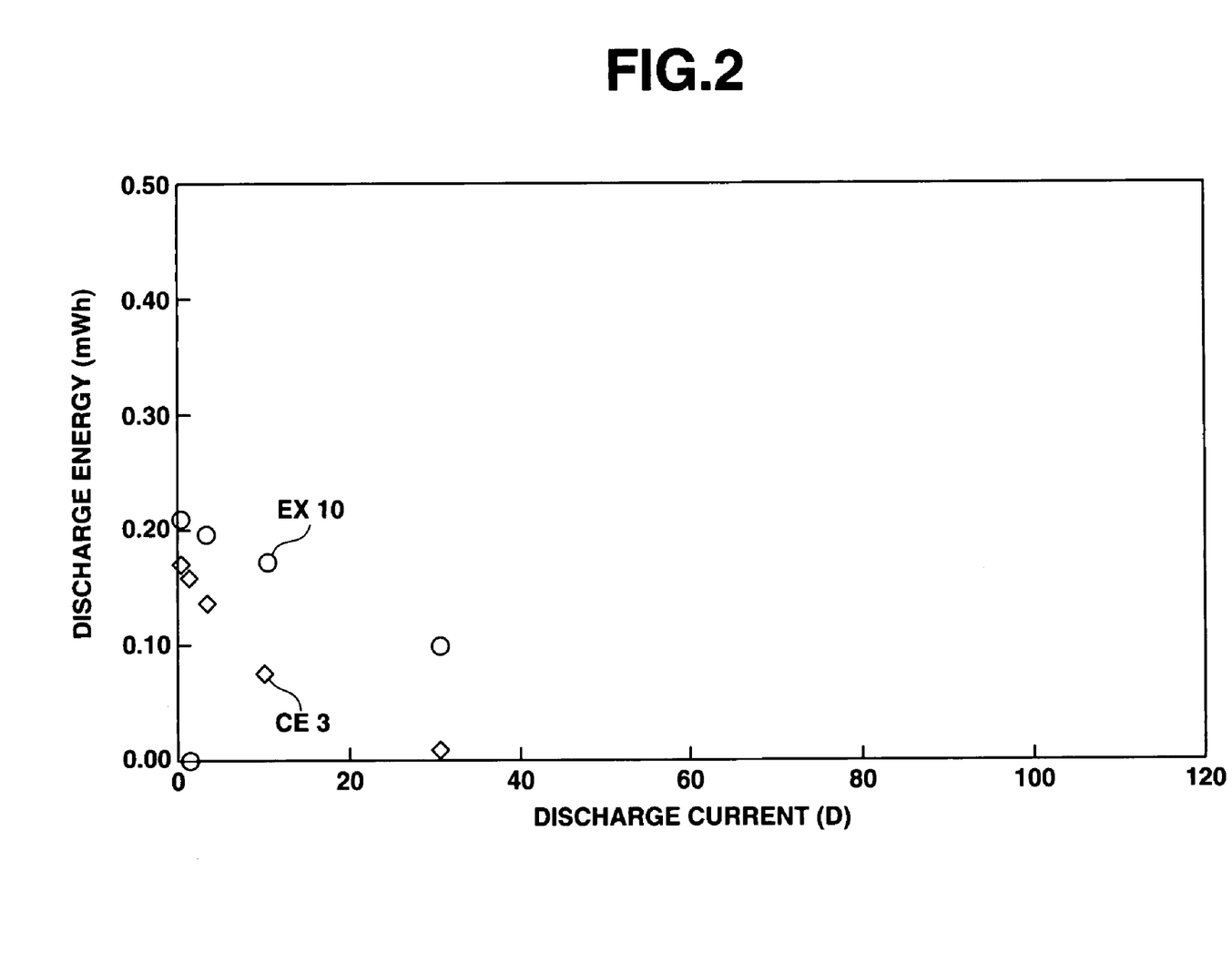
FIG. 2 is a graph showing the discharge current dependence of the discharge energy in the electrical double-layer capacitors in Example 10 of the invention and in Comparative Example 3.

It is apparent from FIG. 2 that the difference between the discharge energies of the respective capacitors grows larger as the discharge current is increased. For example, at a discharge current of 10 D, the discharge energy by the capacitor in Example 10 is about 2.5 times the discharge energy of the capacitor in Comparative Example 3.

Figure 3:
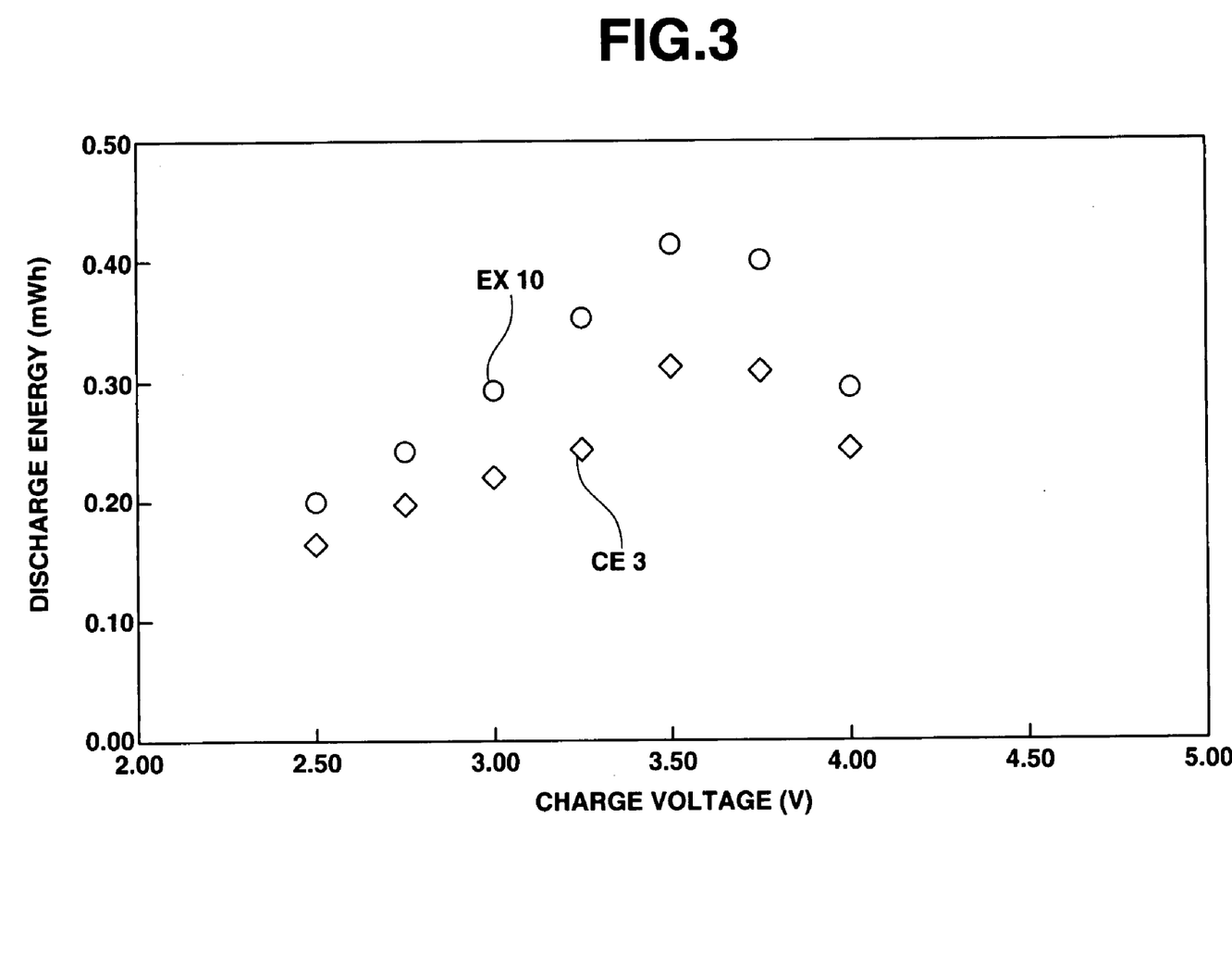
FIG. 3 is a graph showing the charge voltage dependence of the discharge energy in the electrical double-layer capacitors in Example 10 of the invention and in Comparative Example 3.

Moreover, it is apparent from FIG. 3 that the difference between the discharge energies of the respective capacitors becomes larger until the charge voltage approaches 3.50 V, with the capacitor in Example 10 having a much larger discharge energy than the capacitor in Comparative Example 3.

Although the reasons for the above are not entirely clear, in addition to moisture removal, electrolysis also leads to the removal of metal ions and other species within the ionic liquid X. Synergistic effects ensuing from such removal may be responsible for these results.

Example 11

Dehydration of Ionic Compound-Containing Organic Solution

Propylene carbonate (PC), vinylene carbonate (VC) and LiPF$_6$ (Kishida Chemical Co., Ltd.) were mixed with a 1.0 M solution of LiPF$_6$ in ethylene carbonate (EC)/diethyl carbonate (DEC)=1:1 (Kishida Chemical Co., Ltd.), thereby preparing a 1.0 M solution of LiPF$_6$ in EC/DEC/PC/VC (100.0/157.1/28.57/2.857 by weight).

Figure 4:
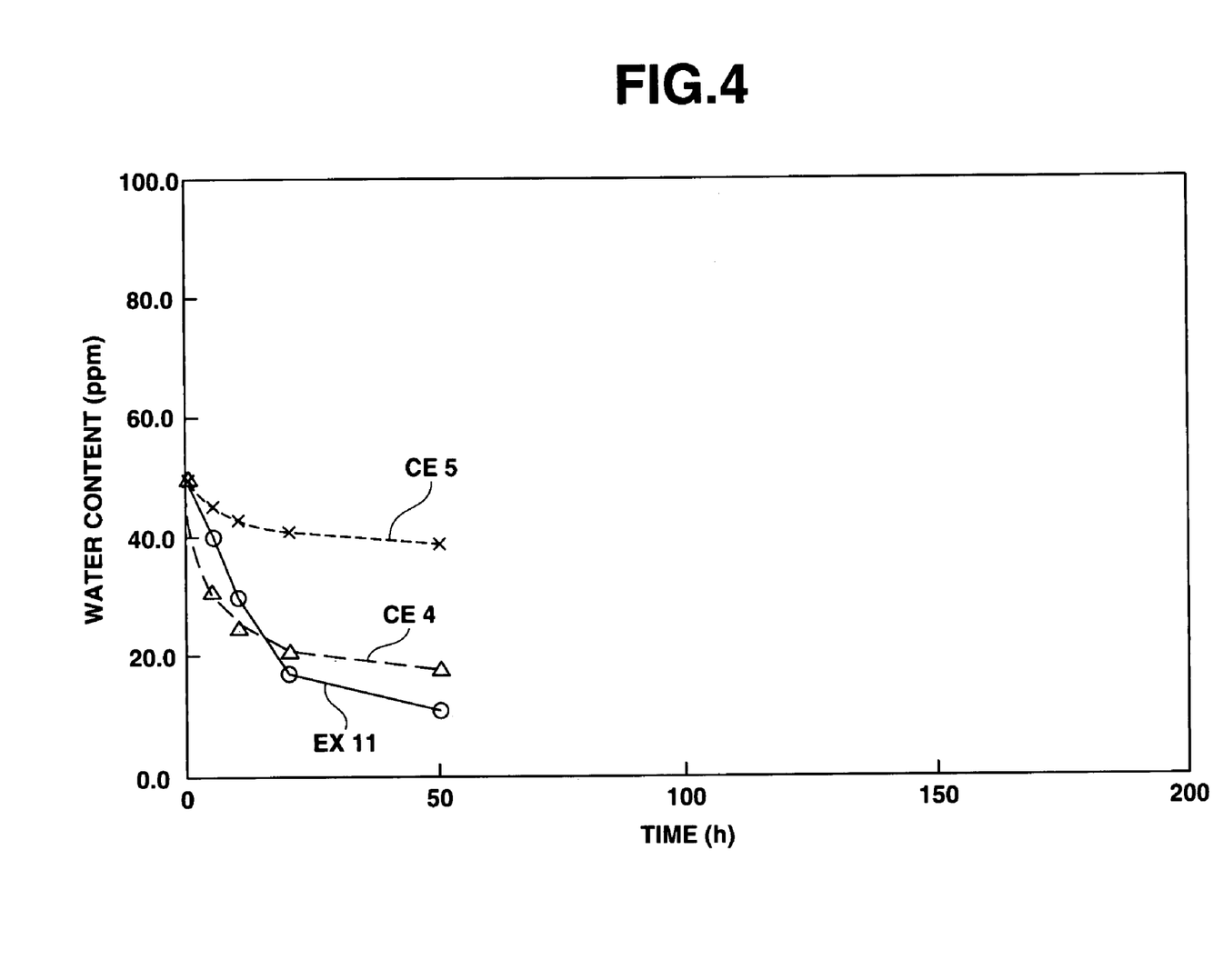
FIG. 4 is a graph showing the change over time in the water content of the liquid electrolytes (organic solutions) in Example 11 of the invention and in Comparative Examples 4 and 5.

This solution was poured into the same type of electrolytic cell as in Example 1, the electrodes were connected to a stabilized power supply (PA18-6A, manufactured by Kenwood KK) at an ambient temperature of about 25° C. and in a dry atmosphere having a dew-point temperature of −50° C., and dehydration was effected by carrying out electrolysis at an upper limit current of 10.0 mA and a voltage setting of 6.0 V, thereby forming a liquid electrolyte (organic solution). The interior of the system was stirred at this time using a magnetic stirrer. FIG. 4 shows the change in water content over time. The final water content was 11 ppm.

Comparative Example 4

The 1.0 M solution of LiPF$_6$ in EC/DEC/PC/VC (100.0/157.1/28.57/2.857 by weight) prepared in Example 11 was dehydrated by bubbling through nitrogen gas, thereby giving a liquid electrolyte. FIG. 4 shows the change in water content over time. The final water content was 18 pm.

Comparative Example 5

The 1.0 M solution of LiPF$_6$ in EC/DEC/PC/VC 100.0/157.1/28.57/2.857 by weight) prepared in Example 11 was left to stand at an ambient temperature of about 25° C. and in a dry atmosphere having a dew-point temperature of −50° C., thereby giving a liquid electrolyte. FIG. 4 shows the change in water content over time. The final water content was 39 pm.

Example 12, Comparative Examples 6 and 7

Secondary Cells

<Production of Positive Electrode>

LiCoO$_2$ (made by Seido Chemical Industry Co., Ltd.) as the positive electrode active material, Ketjenblack EC (made by Lion Corporation) as the conductive material, polyvinylidene fluoride (PVDF 1300, made by Kureha Chemical Industry Co., Ltd.) and the polyurethane resin solution prepared in Synthesis Example 3 were mixed in a weight ratio of 100.0:4.35:4.13:2.72, respectively, then dissolved or dispersed and mixed in 1-methyl-2-pyrrolidone (NMP; 56.74 parts by weight per 100 parts by weight of LiCoO$_2$; produced by Wako Pure Chemical Industries, Ltd.) to form a slurry.

The slurry was applied onto an aluminum sheet (thickness, 0.020 mm; made by Nippon Foil Manufacturing Co., Ltd.), then dried, rolled, and cut to dimensions of 50.0 mm (width of coated area, 40.0 mm)×20.0 mm and 50.0×270.0 mm to give positive electrodes. Electrodes having a weight of 0.280 g and a thickness of 0.080 mm were selected and used.

<Production of Negative Electrode>

Mesophase microbeads (made by Osaka Gas Chemicals Co., Ltd.) as the negative electrode active material and polyvinylidene fluoride (PVdF 900, made by Kureha Chemical Industry Co., Ltd.) were mixed in a weight ratio of 100.0:8.70, respectively, then dissolved or dispersed and mixed in NMP (121.7 parts by weight per 100 parts by weight of mesophase microbeads) to form a slurry.

The slurry was applied onto copper foil (thickness, 0.010 mm; made by Nippon Foil Manufacturing Co., Ltd.), then dried, rolled, and cut to dimensions of 50.0 mm (width of coated area, 40.0 mm)×20.0 mm to give negative electrodes.

<Production of Electrode Group>

An electrode-group was formed by combining two of the above positive electrodes and two of the above negative electrodes with two intervening cellulose separators (TF40-35, made by Nippon Kodoshi Corporation; thickness, 0.035 mm) cut to dimensions of 54.0×22.0 mm.

<Production of Secondary Cell>

The liquid electrolytes prepared in Example 11 and Comparative Examples 4 and 5 were poured into the electrode group fabricated as described above in amounts of 100.0 vol % with respect to the spatial volume of the electrode group. The electrolyte-filled electrode group was then laminate-packed, giving the secondary cells in Example 12 and Comparative Examples 6 and 7.

In these secondary cells, the electrical capacity of the positive electrode active material calculated from a theoretical capacity of 137 mAh/g when x=0.5 in the Faraday reaction $$LiCoO_2 \rightarrow Li_xCoO_2+(1-x)Li^++(1-x)e^-$$

at the positive electrode active material of the cell was taken as the rated capacity of the cell. This was defined as a state of charge of 100.0% (about 36.0 mAh).

The secondary cell was initially charged to 1.50 V at a current of 0.01C, then charged to 3.20 V at a current of 0.05C.

The cell was then subjected to three charge/discharge cycles, each cycle consisting of constant-current/constant-voltage charging to a voltage setting of 4.20 V and a current cut-off of 0.10C, one hour at rest, constant-current discharging at 1.00C to a voltage cut-off of 3.0 V, and one hour at rest. This was followed by constant-current discharge at a current of 0.20C to 2.75 V, thus placing the sample cell in an initial state (SOC=0%). In particular, the initial capacity of each secondary cell was taken to be the sum of the 1.00C discharge in the third cycle and the 0.20C discharge.

Figure 5:
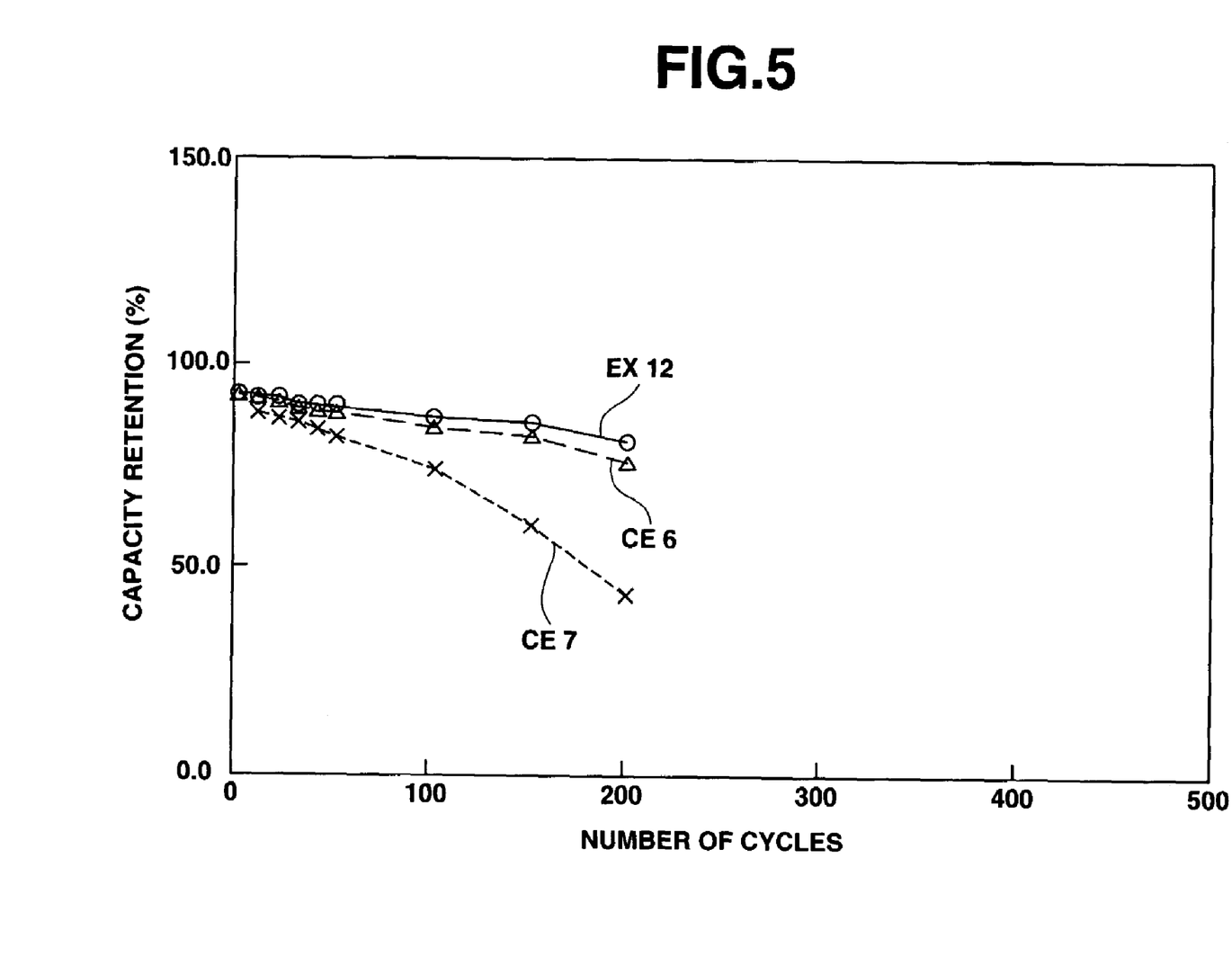
FIG. 5 is a graph showing the cycle life of the secondary cells in Example 12 of the invention and in Comparative Examples 6 and 7.

Cycle life tests were then carried out in which each cycle consisted of constant-current/constant-voltage charging to a voltage setting of 4.20 V and a current cut-off of 0.10C and constant-current discharging at 1.00C to a voltage cut-off of 3.0 V. The changes in capacity for the respective secondary cells were compared. The results are shown in FIG. 5.

As shown in FIG. 4, the liquid electrolyte in Example 11 from which moisture was been removed by electrolysis had a lower water content (11 ppm) than the liquid electrolytes in Comparative Example 4 (18 ppm) and Comparative Example 5 (39 ppm). The secondary cell produced in Example 12 using this liquid electrolyte had a capacity retention after 200 charge/discharge cycles of about 82%, which was better than the value of about 77% obtained for the secondary cell in Comparative Example 6 and the value of about 46% obtained for the secondary cell in Comparative Example 7, demonstrating the advantageous effects of water removal.

As described above, the present invention uses electrolysis to remove water from ionic liquids and other liquid electrolytes, making it possible to obtain highly dehydrated ionic liquids and ionic compound-containing organic solvents.

Moreover, by using an ionic liquid or the like as the electrolyte, electrical storage devices (secondary cells, electrical double-layer capacitors, and other types of capacitors) having a high charge/discharge capacity or electrostatic capacitance can be obtained.

The invention claimed is:

1. An ionic liquid containing cations and anions, which liquid is characterized by being an onium salt and having a water content of not more than 150 ppm and being in a liquid state at a temperature not above 25° C.

2. The ionic liquid of claim 1 which is characterized by having a water content of not more than 50 ppm.

3. The ionic liquid of claim 1 which is characterized in that the cation is a quaternary ammonium ion of general formula (1) below (wherein $R^1$ to $R^3$ are each independently an alkyl of 1 to 5 carbons, and any two from among $R^1$, $R^2$ and $R^3$ may together form a ring; and R' is methyl or ethyl).

4. The ionic liquid of claim 3 which is characterized in that the quaternary ammonium ion is $(CH_3)(C_2H_5)_2(CH_3OC_2H_4)N^+$.

5. The ionic liquid of claim 1 which is characterized in that the anion is at least one selected from among $BF_4^-$, $PF_6^-$, $ClO_4^-$, $CF_3SO_3^-$, $CF_3CO_2^-$ and $(CF_3SO_2)_2N^-$, and has a theoretical decomposition voltage of at least 1.23 V.

6. An electrical double-layer capacitor having a pair of polarizable electrodes, a separator between the polarizable electrodes and a liquid electrolyte, which electrical double-layer capacitor is characterized in that the liquid electrolyte contains the ionic liquid of claim 1 and an organic solvent having a water content of not more than 50 ppm.

7. A secondary cell having a positive electrode, a negative electrode, a separator between the positive and negative electrodes, and a liquid electrolyte, which secondary cell is characterized in that the liquid electrolyte contains the ionic liquid of claim 1 and an organic solvent having a water content of not more than 50 ppm.

* * * * *